United States Patent [19]
Abuto et al.

[11] Patent Number: 5,788,684
[45] Date of Patent: Aug. 4, 1998

[54] LIQUID-ABSORBING ARTICLE

[75] Inventors: Frank Paul Abuto; Debra Nell Welchel, both of Alpharetta; Carmen Elissa Sullivan, Dunwoody, all of Ga.

[73] Assignee: Kimberly-Clark Worldwide, Inc., Neenah, Wis.

[21] Appl. No.: 614,028

[22] Filed: Mar. 12, 1996

Related U.S. Application Data

[63] Continuation of Ser. No. 298,819, Aug. 31, 1994, abandoned.

[51] Int. Cl.$^6$ .................................................. A61F 13/15
[52] U.S. Cl. .................... 604/368; 604/378; 604/385.1; 604/358
[58] Field of Search .................... 604/358, 369, 604/378, 379, 380, 368, 383, 372, 385.1

[56] References Cited

U.S. PATENT DOCUMENTS

| | | | |
|---|---|---|---|
| 3,214,323 | 10/1965 | Russell et al. | 604/368 |
| 3,441,023 | 4/1969 | Rijssenbeek | 604/378 |
| 3,612,055 | 10/1971 | Mesek et al. | 128/287 |
| 3,889,679 | 6/1975 | Taylor | 604/378 |
| 4,055,180 | 10/1977 | Karami | 128/287 |
| 4,276,338 | 6/1981 | Ludwa et al. | 428/137 |
| 4,327,728 | 5/1982 | Elias | 604/368 |
| 4,333,979 | 6/1982 | Sciaraffa et al. | 604/380 |
| 4,381,783 | 5/1983 | Elias | 604/368 |
| 4,443,512 | 4/1984 | Delvaux | 604/379 |
| 4,699,620 | 10/1987 | Bernardin | 604/385 |
| 5,118,376 | 6/1992 | Pigneul et al. | 156/219 |
| 5,147,343 | 9/1992 | Kellenberger | 604/368 |
| 5,175,046 | 12/1992 | Nguyen | 428/198 |
| 5,294,478 | 3/1994 | Wanek et al. | 428/218 |
| 5,336,552 | 8/1994 | Strack et al. | 428/224 |
| 5,352,217 | 10/1994 | Curro | 604/378 |
| 5,409,476 | 4/1995 | Coates | 604/391 |

FOREIGN PATENT DOCUMENTS

| | | |
|---|---|---|
| 2 114 815 | 8/1994 | Canada. |
| 0 146 190 | 6/1985 | European Pat. Off.. |
| 0 558 889 | 9/1993 | European Pat. Off.. |
| 2089214 | 6/1982 | United Kingdom ............ 604/380 |
| 2 174 037 | 10/1986 | United Kingdom. |
| 2 266 465 | 11/1993 | United Kingdom. |
| 87/00057 | 1/1987 | WIPO. |

*Primary Examiner*—John G. Weiss
*Assistant Examiner*—Dennis Ruhl
*Attorney, Agent, or Firm*—Patrick C. Wilson

[57] ABSTRACT

The present invention is directed to a liquid-absorbing article which employs a high absorbency material such as superabsorbent particles. The particles are housed within discrete chambers formed within an absorbent core so as to provide access to incoming liquid and ample area for the particles to expand as they absorb the incoming liquid.

21 Claims, 6 Drawing Sheets

LIQUID-ABSORBING ARTICLE

This application is a continuation of application Ser. No. 08/298,819 entitled "LIQUID-ABSORBING ARTICLE" and filed in the U.S. Patent and Trademark Office on Aug. 31, 1994, now abandoned. The entirety of this application is hereby incorporated by reference.

FIELD OF THE INVENTION

The present invention is directed to a liquid-absorbing article. More specifically, the present invention is directed to a liquid-absorbing article which has particular suitability as an absorbent system for use in personal care absorbent products such as diapers, training pants, sanitary napkins, incontinence garments, bandages and the like.

BACKGROUND OF THE INVENTION

As advancements in liquid absorption progress, the understanding of the various materials and components used to absorb liquids and their interaction have greatly increased. This is especially true with respect to the absorbent systems used in personal care absorbent products. Using disposable diapers as an example, originally the design of such diapers used wood pulp fluff as the sole material for absorbing liquid, in this case urine. The problem with wood pulp fluff, however, was its poor wet strength and its tendency to collapse when wet which in turn often resulted in diaper leakage.

As the advances in diaper construction progressed, high absorbency materials such as superabsorbents were mixed in with the wood pulp fluff to increase the overall liquid retention capacity of the diaper's absorbent core. This in turn allowed for a reduction in the overall thickness of the diaper by removing a portion of the wood pulp fluff and supplanting it with higher and higher quantities of the superabsorbent. Despite the decrease in the overall size of the absorbent core and the increase in the overall liquid retention capacity, there was still a problem with the ability of the diaper's absorbent core to accept rapid influxes of urine, especially on second, third and fourth insults, without the risk of the urine pooling on the surface and running off. One source of this problem was the superabsorbent itself.

To permit rapid uptake of liquid in an absorbent core of a diaper or other personal care absorbent product, there must be sufficient interstitial spacing between the fibers to permit fluid transport. Unfortunately, many superabsorbents swell as they absorb liquid thereby closing the interstitial spaces and causing a phenomenon known as "gel blocking". Once gel blocking has occurred, rapid liquid transport through the gel blocked area is difficult.

To assist in correcting this problem and to further attempt to reduce the pooling of rapidly deposited liquid on the surface of the diaper, several other advancements were designed. One was the selective placement of the superabsorbent within localized regions of the absorbent core as, for example, in an interior layer within the absorbent core or in discrete pockets as shown in U.S. Pat. No. 4,055,180 to Karami. Another solution was the inclusion of additional layers within the diaper, oftentimes above the absorbent core to act as a dashpot or temporary reservoir for the incoming liquid until such time as the absorbent core had time to fully absorb the liquid. These added layers once again increased the overall thickness of the diaper which was contrary to the general trend to make such products as thin as possible. Another problem with using multiple layers was the transport of liquid across the interfaces of the two materials. It has been found that liquids frequently have difficulty transferring from one material to another because of problems at the interface between the two materials. It therefore would be desirable if more of this liquid transfer could take place within the same general horizontal plane within the diaper or other personal care absorbent product so as to minimize the transfer of liquid across the interfaces of adjacent but different materials in the vertical direction.

Another problem when using superabsorbents is their need to swell or expand as they absorb liquid. If the particles are too closely confined, the particles cannot freely expand, and/or the swelled particles can cause rupturing of the materials around them which in turn can allow the superabsorbent to ooze out and possibly come in contact with the wearer. Consequently, there is a need for an improved liquid-absorbing article containing a high absorbency material which can readily accept and retain deposited liquids.

SUMMARY OF THE INVENTION

The present invention is directed to a liquid-absorbing article which has particular suitability as an absorbent system for use in personal care absorbent products such as diapers, training pants, sanitary napkins, incontinence garments, and the like. In its most basic design, the liquid-absorbing article according to the present invention includes a liquid permeable top sheet and a bottom sheet with an absorbent core disposed therebetween. The absorbent core defines a plurality of apertures therein which extend from the top surface of the absorbent core through the absorbent core to a bottom surface thereof. The top surface is attached to the top sheet and the bottom surface of the absorbent core is attached to the bottom sheet. A high absorbency material is located within at least a portion of the apertures. In more refined embodiments, the top sheet and/or bottom sheet can be releasably attached to the absorbent core by attachment means. The attachment means can provide a bond strength between the absorbent core and either the top sheet or the bottom sheet which is less than the swelling force exerted on the top sheet or the bottom sheet when the high absorbency material is exposed to an aqueous liquid. As a result, the top sheet or bottom sheet will delaminate from the absorbent core before the top sheet or bottom sheet ruptures from the swelling force.

The absorbent core can be designed to have a number of specifically tailored properties including a density of less than 0.08 grams per cubic centimeter, a Frazier air permeability greater than 60 cubic meters per square meter per minute, a thickness under a pressure of 0.3 kilopascals of at least 0.5 centimeters, and a specific volume at zero load which is greater than 18 cubic centimeters per gram. The density, Frazier air permeability, thickness and specific volume at zero load are calculated from a portion of the absorbent core material which is devoid of the plurality of apertures and the high absorbency material.

In other embodiments of the present invention, the absorbent core may have a plurality of densified areas. If desired, these densified areas may extend between and connect at least a portion of the plurality of apertures so as to further aid lateral movement of the liquid to be absorbed across the x-y plane of the structure.

In further embodiments of the present invention, the absorbent core may be comprised of a fibrous nonwoven web in which all or a portion of the fibers are bicomponent fibers.

In still a further embodiment of the present invention, the liquid-absorbent article can include a liquid permeable top sheet and a bottom sheet with an absorbent core disposed therebetween. The absorbent core can include a first portion and a second portion in vertical registry with one another. The first portion can be attached to the top sheet and can define a first plurality of apertures therein and extending therethrough. The second portion can be attached to the bottom sheet and can define a second plurality of apertures therein and extending therethrough. In one configuration the first and second plurality of apertures can be in a vertical registry with one another so that the apertures extend completely through the absorbent core from the top surface through to the bottom surface. In another configuration of the invention, all or a portion of the first and second plurality of apertures can be skewed from one another and therefore not be in vertical registry with one another. As a result, the first and second plurality apertures may be filled with the same or different types of high absorbency materials. For example, the first plurality of apertures may be filled with a high absorbency material which has an absorption rate as measured by the vortex time test which is faster than the high absorbency material filling the second plurality of apertures. Conversely, the first plurality of apertures may be filled with a high absorbency material which has an absorption rate which is slower than the absorption rate of the high absorbency material filling the second plurality of apertures.

In order to facilitate fluid flow through the absorbent core, the first and second portions of the absorbent core may be made from materials which have different densities. For example, the first portion of the absorbent core, which is adjacent the top sheet and therefore closest to the location of an initial liquid contact, can have a lower density and thus a more open structure so as to be able to rapidly take-up fluids and hold them to prevent liquid run-off from the surface of the overall structure. In contrast, the second portion, which is generally disposed away from the direction of the fluid insult, may be made from a material which has a higher density and therefore a greater ability to distribute liquids laterally through the structure so as to maximize the utilization of the overall structure by directing liquid to high absorbency material contained in apertures which are remote from the site of liquid insult. To further enhance this lateral fluid flow, it is also possible to create one or more densified areas in the absorbent core as the densified areas will typically improve lateral fluid flow. Thus, for example, the densified areas may extend between and connect at least a portion of the plurality of apertures to further channel liquid from one aperture to another.

The liquid-absorbing article may be used by itself or it may be incorporated into other structures such as personal care absorbent articles which include, but are not limited to, diapers, training pants, incontinence devices, sanitary napkins, bandages and the like. Typically such personal care absorbent articles will include a bodyside liner for placement adjacent the wearer's skin and a backside liner which is typically liquid impermeable. Disposed between the bodyside liner and the backside liner is an absorbent material whose function it is to absorb and retain liquid passed to it through the bodyside liner. If so desired, the liquid-absorbing article of the present invention may be utilized as the absorbent material in such a personal care absorbent article.

DETAILED DESCRIPTION OF THE INVENTION

Figure 1:
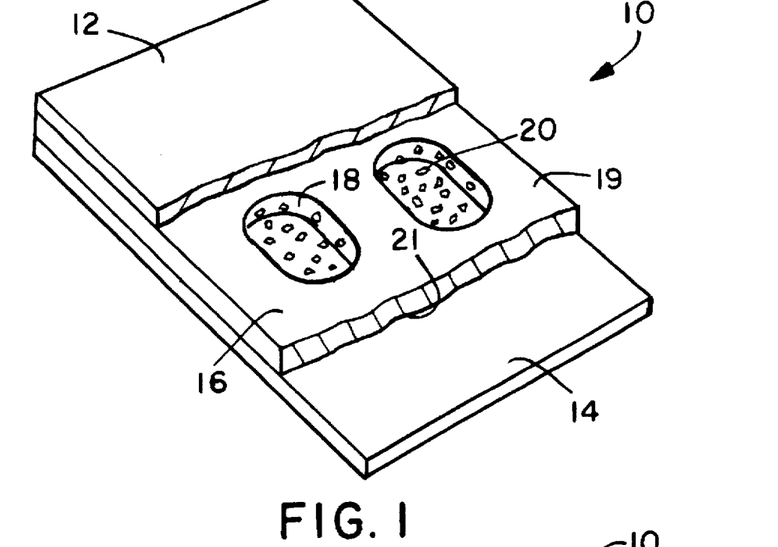
FIG. 1 is a perspective cut-away view of a liquid-absorbing article according to the present invention.
Figure 2:
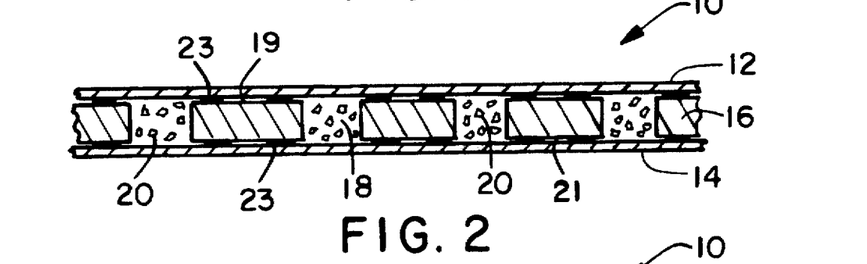
FIG. 2 is a cross-sectional side view of a liquid-absorbing article according to the present invention.

Referring to FIGS. 1 and 2, there is shown a liquid-absorbing article 10 according to the present invention. For purposes of illustration only, the liquid-absorbing article 10 according to the present invention will be described in conjunction with its use in personal care absorbent products or articles including diapers, training pants, incontinence garments, sanitary napkins, bandages and the like. It should be understood that these uses are illustrative only as the scope of the present invention is intended to encompass any use where liquid absorption and retention is required.

The liquid-absorbing article 10 includes a liquid permeable top sheet 12, a bottom sheet 14 and an absorbent core 16 disposed between the top sheet 12 and bottom sheet 14. The absorbent core 16 has a plurality of apertures 18 which extend all the way through the absorbent core 16 from its top surface 19 through to its bottom surface 21. The top surface 19 is attached to the top sheet 12 and the bottom surface 21 is attached to the bottom sheet 14 by suitable attachment means 23 as will be explained in greater detail below. Disposed within the apertures 18 is a high absorbency material 20 commonly referred to as a superabsorbent, material or hydrogel. Such materials are collectively referred to herein as a "high absorbency material" or a "superabsorbent". The high absorbency material 20 is contained within the apertures 18 by the top sheet 12 and bottom sheet 14. A superabsorbent is a water-swellable, water-soluble organic or inorganic material capable, under the most favorable conditions, of absorbing at least about 20 times its weight and, more desirably, at least about 30 times its weight in an aqueous solution containing 0.9 weight percent sodium chloride. Organic materials suitable for use as a superabsorbent material in conjunction with the present invention can include natural materials such as agar, pectin, guar gum, and the like; as well as synthetic materials, such as synthetic hydrogel polymers. Such hydrogel polymers include, for example, alkali metal salts of polyacrylic acids, polyacrylamides, polyvinyl alcohol, ethylene maleic anhydride copolymers, polyvinyl ethers, methyl cellulose, carboxymethyl cellulose, hydroxypropylcellulose, polyvinylmorpholinone; and polymers and copolymers of vinyl sulfonic acid, polyacrylates, polyacrylamides, polyvinylpyrridine, and the like. Other suitable polymers include hydrolyzed acrylonitrile grafted starch, acrylic acid grafted starch, and isobutylene maleic anhydride polymers and mixtures thereof. The hydrogel polymers are preferably lightly crosslinked to render the materials substantially water insoluble. Crosslinking may, for example, be accomplished by irradiation or by covalent, ionic, van der Waals, or hydrogen bonding. The superabsorbent materials may be in any form suitable for use in absorbent composites including particles, fibers, flakes, spheres, and the like. Such superabsorbents are usually available in particle sizes ranging from about 20 to about 1000 microns.

Prior to the present invention, attempts to employ superabsorbents within localized and discrete areas within an absorbent core involve encapsulating small discrete quantities of these superabsorbent particles in localized areas between a top sheet and a bottom sheet which were glued or otherwise attached to one another in the areas between the pockets of superabsorbent. The top sheets and bottom sheets did little to distribute liquid between the localized pockets of superabsorbent due to their thin nature and relatively weak structure. In addition, many types of superabsorbents have large retention capacities but do not quickly absorb liquid. Consequently, the thin top and bottom sheets were inadequate to quickly absorb, store and then transfer or discharge the liquid to the superabsorbent particles. As a result, such absorbent structures often did not perform adequately, especially when used in such personal care absorbent articles as diapers. In addition, if the top and bottom sheets were not made strong enough, and/or if the pockets were packed too tightly with superabsorbent, the top and bottom sheets could restrict the expansion of the superabsorbent or conversely, the top and bottom sheets could rupture thereby allowing the superabsorbent to escape from the pockets - a result that is commonly not desired.

The liquid-absorbing article 10 of the present invention among its other attributes, employs an absorbent core 16 disposed between the top sheet 12 and bottom sheet 14. The apertures 18 in the absorbent core 16 provide small chambers within which to house the high absorbency material or superabsorbent 20. As a result of the use of the absorbent core 16, there is much more room especially in the vertical direction or Z-axis for the superabsorbent particles to expand prior to their exerting a force against the top and bottom sheets 12 and 14 respectively. In addition, as will be described in greater detail below, the absorbent core 16 can be made from a material or materials which will quickly absorb a liquid insult, distribute the liquid insult laterally throughout the layer and give up the liquid to the superabsorbent particles contained within the apertures 18. Consequently, a more efficient overall product can be produced.

The top sheet 12 should be liquid permeable and can be either hydrophilic or hydrophobic though the pore size of the structure should be smaller than the particle size of the superabsorbent particles 20 to reduce dusting or filtering out of the superabsorbent particles. This pore size limitation is not critical when the superabsorbent contained within the apertures 18 is in the form of larger flakes or fibers. The basis weight of the top sheet will generally be dependent upon end use requirements. The top sheet 12 may be made from any suitable material including tissue, apertured films and fibrous nonwovens such as meltblown nonwoven webs, spunbond nonwoven webs and bonded carded nonwoven webs. When the liquid-absorbing article 10 is used in conjunction with personal care absorbent articles, the top sheet 12 will typically have a basis weight of at least about 6 grams per square meter. The other requirement of the top sheet 12 is that it should be bondable or otherwise attachable to the absorbent core 16 and the bottom sheet 14.

The bottom sheet 14 may be the same as or different from the top sheet 12 in construction. The bottom sheet 14 unlike the top sheet 12 does not have to be liquid permeable and, in some cases, it may be desirable that the bottom sheet 14 not be liquid permeable. For example, the bottom sheet 14 could form the outer cover of a personal care absorbent article such as a diaper thereby reducing the overall thickness of the product. In such situations, the bottom sheet 14 can be made from a plastic film with the absorbent core 16 disposed between the bottom sheet 14/outer cover of the diaper and the top sheet 12. To facilitate greater liquid retention, it is desirable that the material or materials from which the bottom sheet 14 is made be bondable or otherwise attachable to the other layers of the structure including the top sheet 12 and absorbent core 16. In addition, the bottom sheet 14 may be designed to aid in liquid distribution laterally through the structure.

Figure 3:
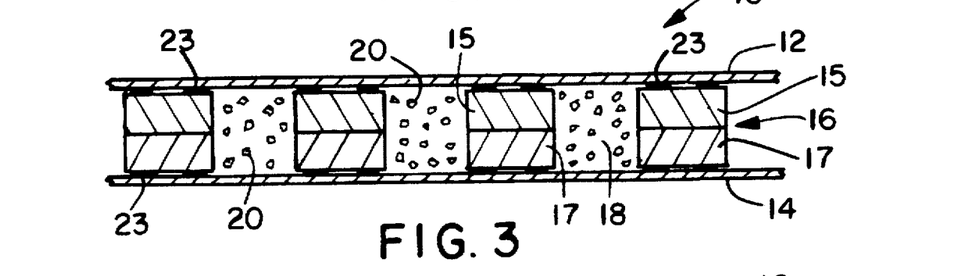
FIG. 3 is a cross-sectional side view of another liquid-absorbing article according to the present invention.
Figure 4:
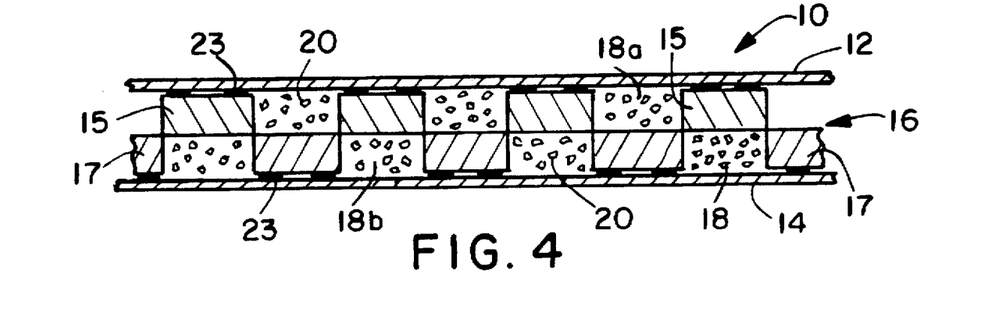
FIG. 4 is a cross-sectional side view of yet another liquid-absorbing article according to the present invention.

The absorbent core 16 can have several different embodiments as shown by the cross-sectional side views of FIGS. 2 through 4 of the drawings. In the most basic design shown in FIG. 2, the absorbent core 16 is a unitary structure whereas in FIGS. 3 and 4, the absorbent core 16 has a first portion 15 and a second portion 17. The first portion 15 and second portion 17 may be part of a single layer or they may be separate layers. As a result, the term "absorbent core" may be a single or multi-layered structure with specific functionalities built into the individual layers or portions.

Returning to FIG. 2, one of the main functions the absorbent core 16 can have is to quickly absorb, retain and then give up the insulted liquid to the high absorbency material 20 located within the plurality of apertures 18 formed within the absorbent core 16. As shown in FIGS. 1 and 2, the apertures extend completely through the absorbent core 16 from its top surface 19 through to its bottom surface 21. If desired, it is also possible to form apertures which only extend partially through the thickness of the absorbent core 16. See FIG. 4. Thus the term "apertures" is meant to include both such configurations. The apertures 18 shown in FIG. 1 are essentially circular in design though any design may be used as, for example, ellipses, squares, diamonds and rectangles. The size, frequency and pattern of the apertures 18 also may be varied to accommodate a particular product design or capacity.

In order to maintain the high absorbency material 20 within the apertures 18, it is desirable that the liquid-permeable top sheet 12 and bottom sheet 14 be secured respectively to the top surface 19 and bottom surface 21 of the absorbent core layer 16 by appropriate attachment means 23. Suitable attachment means 23 can include, but are not limited to, adhesives, thermal bonding and ultrasonic bonding. When securing the top sheet 12 and bottom sheet 14 to the absorbent core 16, care should be taken to monitor the swelling forces that the high absorbency material 20 may exert on the top sheet 12 and bottom sheet 14. As was mentioned above, it is possible to make the top sheet 12, for example, from a thin sheet of paper tissue which often weakens when it becomes wet. If the pressure exerted by the swelling high absorbency material 20 on the top sheet 12 is too great, it could cause the tissue top sheet 12 to rupture which is generally undesirable. As a result, it may be desirable to select an attachment means 23 which releasably attaches the top and bottom sheets to the absorbent core by providing a bond strength between the absorbent core 16 and either the top sheet 12 or the bottom sheet 14 which is less than the swelling force exerted by the high absorbency material 20 on the top sheet 12 or bottom sheet 14. Thus, when the high absorbency material 20 is exposed to an aqueous liquid the bond strength is designed so the top sheet or bottom sheet will delaminate from the absorbent core 16 before the top sheet or bottom sheet ruptures from the swelling force. This can be accomplished, for example, by selecting an adhesive with a low bond strength, applying minimal quantities of adhesive or applying the adhesive in select locations. Alternatively, when using thermal bonding or ultrasonic bonding, the degree of bonding and the surface area of the bonding can be adjusted to achieve the same results.

Turning to FIGS. 3 and 4 there is shown a more elaborate absorbent core 16. As shown in these Figures the absorbent core 16 includes a first portion 15 and a second portion 17. Though not shown, it is also within the scope of the present invention to provide even more layers, portions or regions within the x-y plane and the z-axis direction of the absorbent core 16 if so desired. In FIG. 3 the first portion 15 has a first plurality of apertures 18a and the second portion 17 has a second plurality of apertures 18b which are in vertical registry with one another. If desired, the first portion 15 can be made from a highly porous material such as a fibrous nonwoven web having a large void volume so that it will quickly absorb any liquids passed to it through the liquid permeable top sheet 12. In contrast, if so desired, the second portion 17 can be made from a material having a more refined pore structure so that the liquid received from the first portion 15 can be controlled and distributed laterally through the structure and greater utilization of the absorbent core 16 can be achieved in the x-y plane of the structure. Typically, to achieve these attributes, the first portion will have a lower density than the second portion. In addition, it has been found that such structures function particularly well when made from fibrous nonwoven webs containing bicomponent fibers. Bicomponent fibers are fibers which utilize two or more polymers, typically with different melting or softening points, in different regions of the fibers. The lower melting point component can be used to bond the fibers together. Absorbent cores made from spunbond bicomponent fiber webs have been found to work particularly well as shown by the examples below. The method for producing such webs is taught in U.S. Pat. No. 5,336,552 to Strack et al. which is incorporated herein by reference in its entirety.

Turning to FIG. 4, there is shown a liquid-absorbing article 10 wherein the apertures 18a in the first portion 15 of the absorbent core 16 are skewed from and therefore are not in vertical registry with the apertures 18b in the second portion 17 of absorbent core 16. This design, among other things, provides greater surface area per volume ratios for individual apertures 18 and thus for liquid contact with the high-absorbency material 20 contained within the apertures 18. Another advantage of the skewed design in FIG. 4 is that the type of high absorbency material 20 within the apertures 18a and 18b can be varied. There are now available a number of types of superabsorbents with various properties. Some superabsorbents absorb liquids more quickly than others while other superabsorbents are able to absorb greater quantities of liquid while under a certain load or pressure, commonly referred to as "high AUL (Absorbency Under Load) superabsorbents." As a result, it may be desirable to fill apertures 18a with one type of superabsorbent 20, such as a fast absorbing superabsorbent, and the lower apertures 18b with another type of superabsorbent or vice versa.

Figure 5:
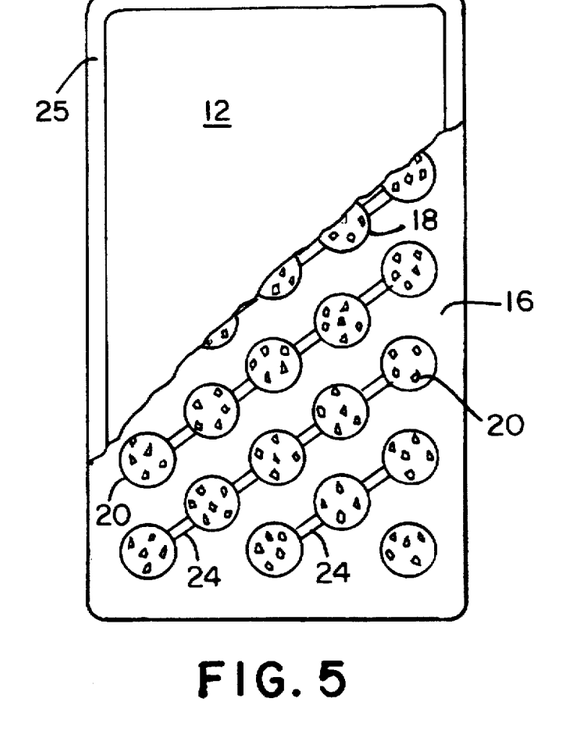
FIG. 5 is a top plan view of the absorbent core portion of a liquid-absorbing article according to the present invention. The absorbent core has embossed channels on its top surface for facilitating liquid transport across the surface of the structure.

As a further refinement to the present invention, the liquid-absorbing article 20 may have a plurality of densified areas such as embossed channels 24 running through at least the absorbent core 16 (see FIG. 5) and, if desired, the top sheet 12 and bottom sheet 14. Such channels 24 can be made by densifying the absorbent core 16 in select areas, as between the apertures 18, through the use of embossing rolls. By connecting the apertures 18 via the channels 24, another means is provided for increasing the lateral flow of liquid across the structure and to as many superabsorbent-containing apertures as possible.

Figure 6:
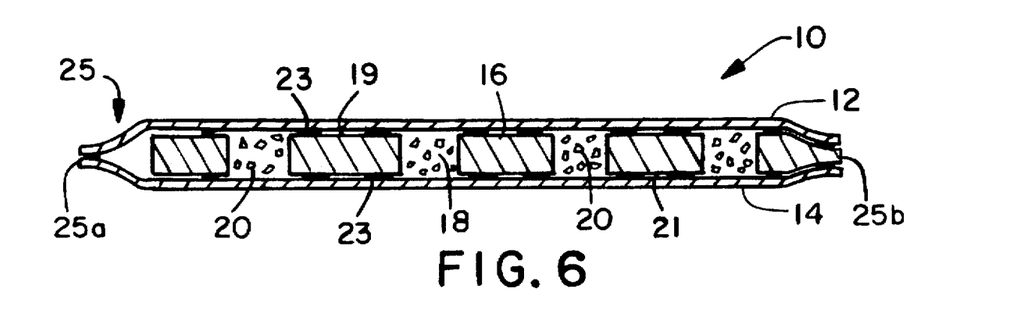
FIG. 6 is a cross-sectional side view of another liquid-absorbing article according to the present invention utilizing a peripheral seal around the exterior edges of the article.

Still a further refinement of the present invention is shown in cross-section in FIG. 6 of the drawings. As stated previously, when the high absorbency material 20 within the apertures 18 is contacted by an aqueous liquid such as water, saline solution or urine, the material 20 will begin to expand and exert forces against the surrounding materials including the top sheet 12 and bottom sheet 14. As a result, it is desirable that the attachment means 23 provide respective bond strengths between the top surface 19 and bottom surface 21 of the absorbent core 16 and the top sheet 12 and bottom sheet 14 which are less than the swelling force exerted on the top sheet 12 or bottom sheet 14 when the high-absorbency material is exposed to an aqueous liquid so that the top or bottom sheet will delaminate from the absorbent core before the top sheet or bottom sheet ruptures from the swelling force. If this delamination occurs, the high absorbency material can begin to migrate through the liquid-absorbing article 10. To prevent the material 20 from leaking out the sides of the article 10, it is desirable that the top sheet 12 and bottom sheet 14 be attached to one another by a peripheral seal 25 which has a greater bond strength than the bond strength between the top sheet 12 and the top surface 19 of the absorbent core 16 or the bottom sheet 14 and the bottom surface 21 of absorbent core 16. In so doing, the top sheet 12 and bottom sheet 14 form an envelope around the absorbent core 16. As shown in FIG. 6, the peripheral seal 25a is directly between the top sheet 12 and bottom sheet 14. It is also possible, however, to form a peripheral seal 25b through the absorbent core material 16. Suitable means for perfecting the peripheral seal 25 include such means as thermal bonding, ultrasonic bonding and adhesives.

Figure 7:
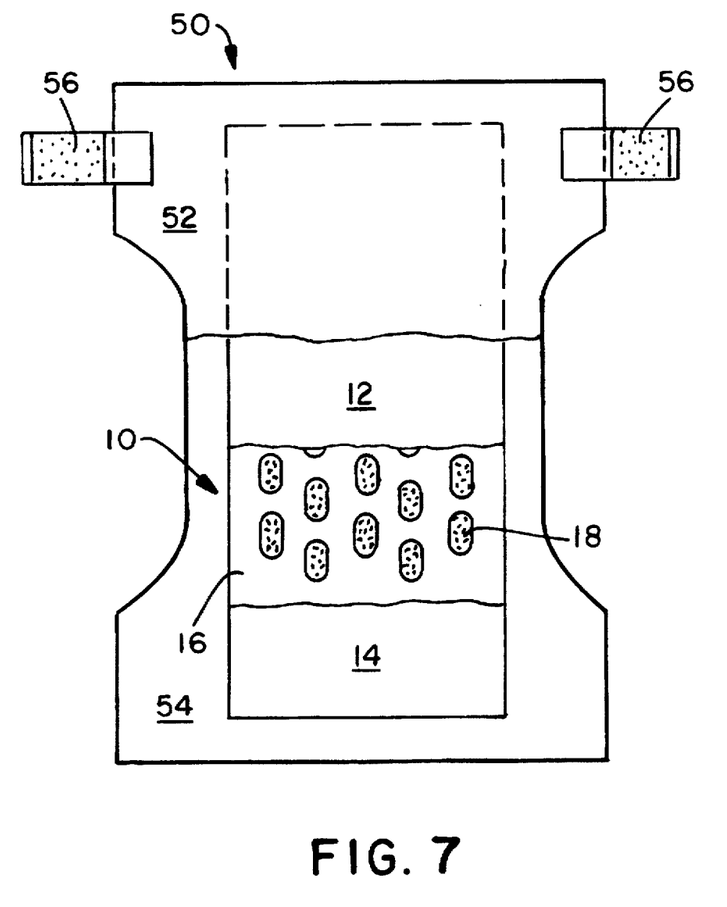
FIG. 7 is a partial cut-away top plan view of a diaper including a liquid-absorbing article according to the present invention.

Turning to FIG. 7, the liquid-absorbing article 10 may be incorporated within a personal care absorbent article 50. For purposes of illustration only, the personal care absorbent article is shown in the form of a diaper. This illustration, however, should not be construed as a limitation as to the scope of the present invention.

The personal care absorbent article 50 in FIG. 7 includes a bodyside liner 52 and a backside liner 54 with the liquid-absorbing article 10 disposed between the bodyside liner 52 and the backside liner 54. To secure the personal care absorbent article 50 about a wearer (not shown), the article is typically provided with some type of fastening means 56 such as diaper fastening tape. The liquid-absorbing article 10 is positioned within the diaper 50 such that the top sheet 12 is positioned adjacent the bodyside liner 52. If desired, the article 10 may be secured within the diaper 50 as by gluing the article 10 to backside liner 54 and/or the bodyside liner 52. The resultant diaper 50 functions well in absorbing liquids especially when exposed to multiple insults.

Having described the present invention in detail, several samples were prepared, measured and tested. The test procedures and examples are set forth below.

TEST PROCEDURES

A series of test procedures are set forth below. These test procedures were used to measure various properties of the present invention.

Frazier Air Permeability

The procedure used to determine Frazier air permeability was conducted in accordance with the specifications of method 5450, Federal Test Methods Standard No. 191 A except that specimen sizes were 8 inches (20 centimeters)×8 inches rather than 7 inches (18 centimeters) ×7 inches. The larger size made it possible to ensure that all sides of the specimen extended well beyond the retaining ring and facilitated clamping of the specimen securely and evenly across the orifice. Values are given in cubic meters per square meter per minute ($m^3/m^2/min$). Further, when calculating the Frazier air permeability of the absorbent core, the value should be calculated for a piece of material which is devoid of the apertures 18 and superabsorbent 20.

Fluid Run-Off Evaluation

Figure 8:
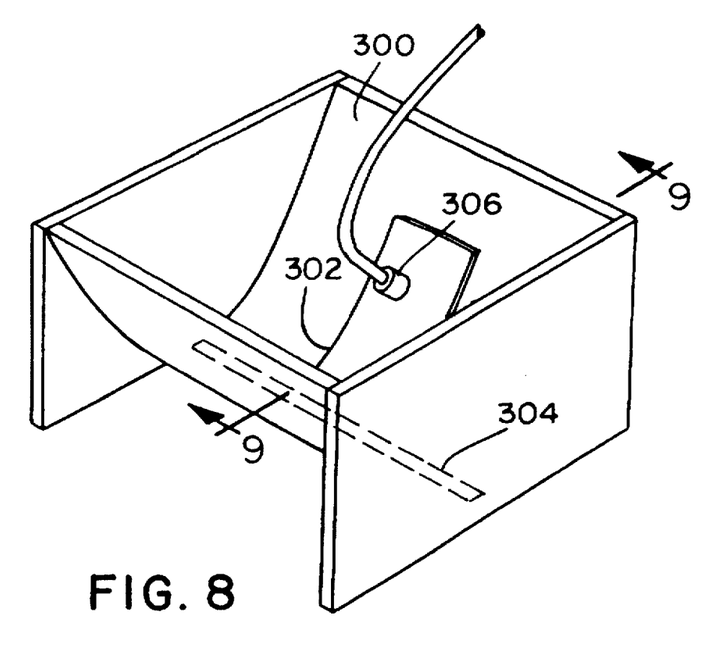
FIG. 8 is a perspective view of the apparatus used in conducting the fluid run-off evaluation test.
Figure 9:
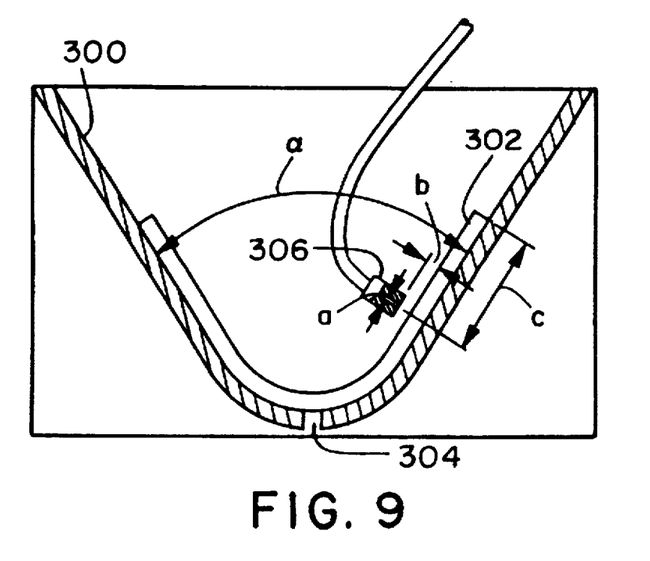
FIG. 9 is a cross-sectional view of the apparatus used in conducting the fluid run-off evaluation test.

For purposes of the present invention, the fluid run-off evaluation is determined by providing a sample which is 15 inches long (38 centimeters) and 4 inches (10 centimeters) wide. Referring to FIGS. 8 and 9, the sample 302 is placed in a trough 300 having an included angle (alpha) of 60°. Trough 300 defines a slot 304 extending across the entire width of the trough 300 at is lowest point. The trough 300 is at least 4 inches (10 centimeters) wider than the sample 302 to be tested. A collection device (not shown) is placed under the trough 300 to collect fluid which passes out of trough 300 through slot 304. FIG. 9 is a cross-sectional view taken along line 6—6 of FIG. 8. As can be seen from reference to FIG. 9, test fluid is delivered to the sample 302 to be tested from a nozzle 306 having a 3 millimeter diameter (a) which is attached to a peristaltic pump equipped with a pulse suppressor. The nozzle is placed a distance (b) of 6.4 millimeters from the surface of the sample to be tested at a distance (c) of about 5.5 inches (14 centimeters) from the end of the sample to be tested such that the nozzle is generally perpendicular to the immediate adjacent surface of the sample 302 to be tested. This positioning should be maintained throughout the test. The sample to be tested is subjected to four 60 milliliter insults of saline solution. The saline solution is applied through the nozzle 306 at a rate of approximately 15 milliliters per second and a velocity of about 210 centimeters per second. Each of the four 60 milliliter insults is applied 15 minutes after the immediately preceding insult. The amount of fluid which passes through slot 304 and which is collected in the collection device, is weighed in grams and is reported for each insult. As a general rule, the lower the amount of run-off per insult, the better the composite would be expected to perform. The saline solution referenced herein was a 0.9 percent certified blood bank stabilized isotonic saline solution containing no preservatives. The saline solution is manufactured by Stephens Scientific Division of Cornwell Corporation of Riverdale, N.J. and is distributed by Baxter Healthcare Corporation, Scientific Products Division of McGraw Park, Ill. under catalog number B3158-1.

Fluid-Intake and Flowback Evaluation (FIFE)

Figures 10, 11:
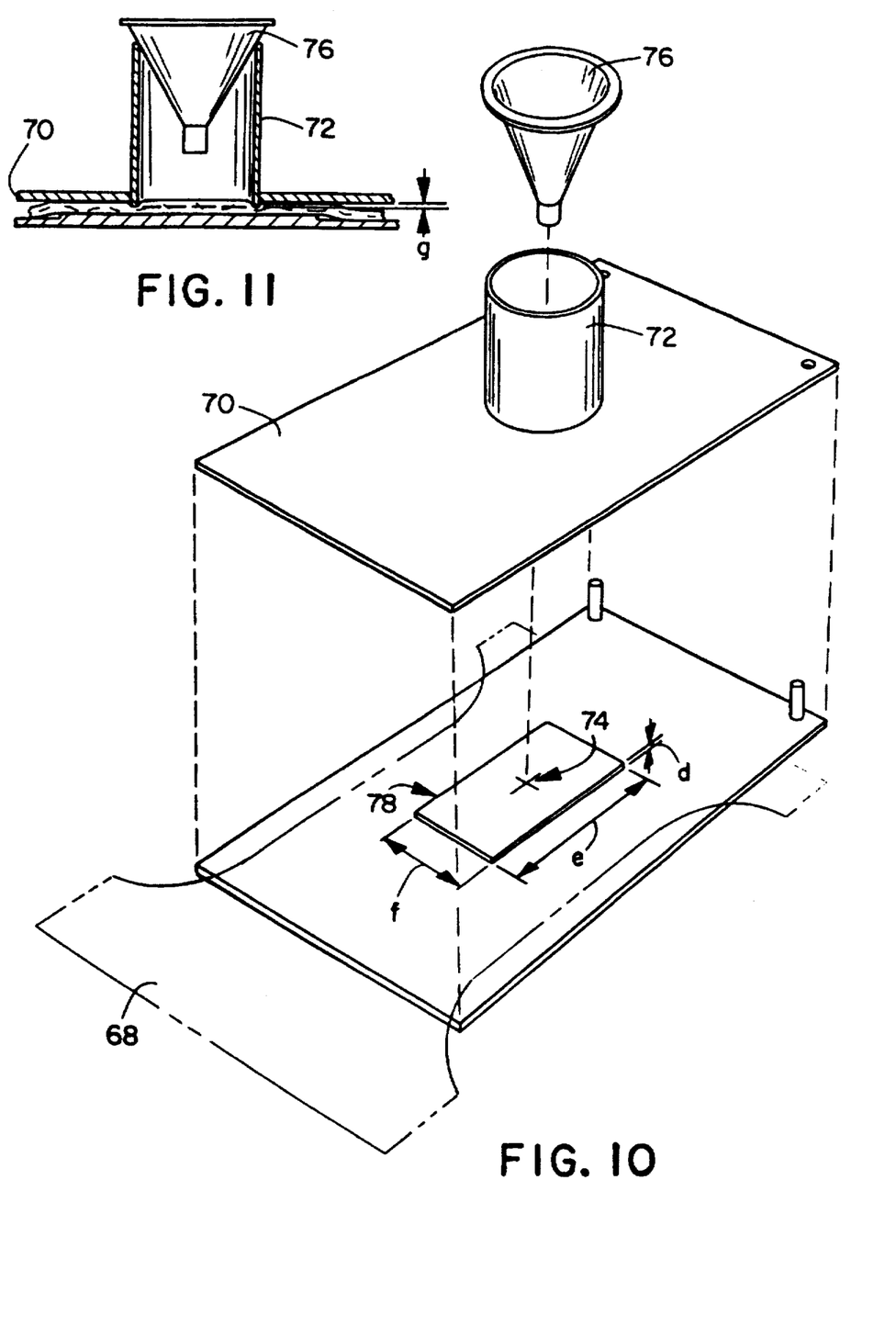
FIG. 10 is an exploded perspective view of a testing apparatus used to measure fluid intake and flowback.
FIG. 11 is a side elevational view showing the apparatus of FIG. 10 in operation.

The apparatus shown in FIGS. 10 and 11 is utilized for this test. The sample to be tested is shown in phantom as reference numeral 68 in FIG. 10. If the sample is in the form of, for example, a diaper as is shown in FIG. 10, the diaper to be tested is prepared by cutting the leg elastic members (not shown) every one inch (2.54 cm) along their length in order for the sample to lie flat. Data reported herein was obtained with 4 inch (10 centimeters) by 15 inch (38 centimeters) sample sizes.

The sample 68 to be tested is placed flat and smooth under an 880 gram cylinder plate assembly 70 such that the cylinder 72 which has a 5.1 centimeter inner diameter, ends up in a designated location 74. Eighty milliliters of the previously described 0.9 percent saline solution is poured through the funnel 76 on top of the cylinder 72. The funnel opening at the bottom had an inner diameter of 7 millimeters. The fluid delivery rate was 22 milliliters per second. The time elapsing between the first fluid contact with the sample and the time when fluid disappears into the sample is measured with a stop watch. One minute after the initial fluid insult is imbibed, a second insult of the same size is introduced. The time to imbibe the fluid is measured as for the first insult.

Figure 12:
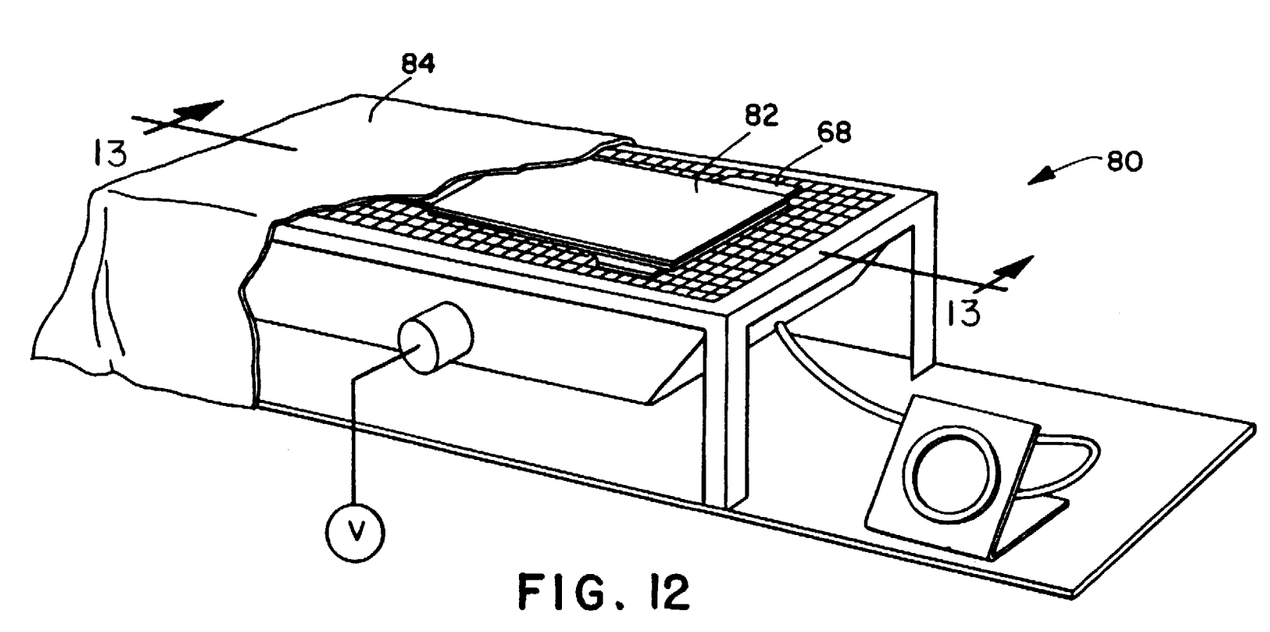
FIG. 12 is a perspective view showing a fluid flowback testing apparatus.
Figure 13:
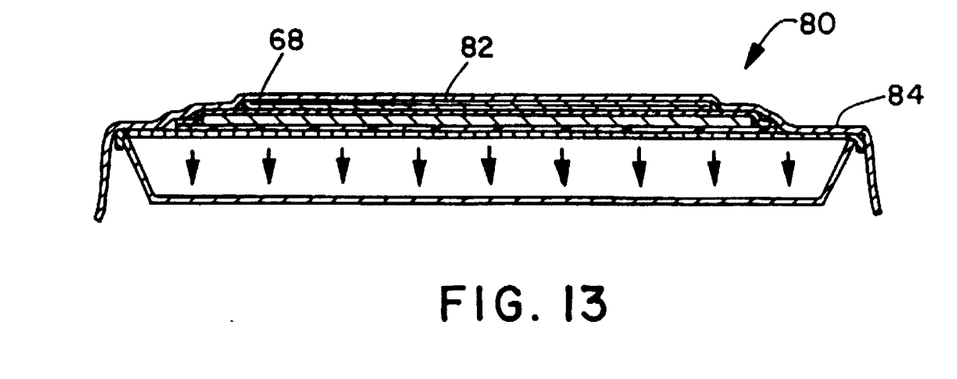
FIG. 13 is a cross-sectional view of FIG. 12 taken along line 10—10.

Referring to FIGS. 12 and 13, one minute after the second insult is imbibed, the sample 68 is placed on a vacuum apparatus 80 and covered with blotter paper 82. A liquid-impervious latex sheeting 84 is then used to cover the blotter paper and sample. A 35,000 dyne per square centimeter (about 0.5 psi) vacuum pressure is then applied to suck the impervious latex sheeting 84 onto the blotter 82 and sample 68 for two minutes. The increase in weight of the blotter paper 82 represents the flowback from the sample and is recorded in grams.

Within one minute after completion of the flowback, a third fluid insult of 80 milliliters is introduced and timed. The fluid intake time is then determined to be the number of seconds for the prescribed amount of fluid to enter the sample.

Thickness and Density

To measure the thickness of a material a five inch by five inch (127 millimeter by 127 millimeter) sample of the material in question is compressed under a load of 0.05 pounds per square inch (3500 dynes per square centimeter) and the thickness is measured while the sample is under this compressive load. Density in turn is calculated by dividing the mass of the sample by the volume which is equal to the thickness (as calculated above) times the surface area of the sample.

Vortex Time

General description:

The vortex test measures the amount of time in seconds required for 2 grams of a superabsorbent material to close a vortex created by stirring 50 milliliters of saline solution at 600 revolutions per minute on a magnetic stir plate. The time it takes for the vortex to close is an indication of the free swell absorbing rate of the superabsorbent material. This test can be used to measure the absorption time of one high absorbency material relative to another.

Equipment and Materials

1. Beaker, 100 milliliters.
2. Programmable magnetic stir plate, capable of providing 600 revolutions per minute (such as that commercially available from PMC Industries, under the trade designation Dataplate® Model #721).
3. Magnetic stir bar without rings, 7.9 millimeters ×32 millimeters, Teflon® covered (such as that commercially available from Baxter Diagnostics, under the trade designation S/P® brand single pack round stirring bars with removable pivot ring).
4. Stopwatch.
5. Balance, accurate to +/−0.01 gram.

6. Saline solution, 0.87 w/w percent, Blood Bank Saline available from Baxter Diagnostics (considered, for the purposes of this application to be equivalent of 0.9 weight percent saline).
7. Weighing paper.
8. Room with standard condition atmosphere: Temperature= 23° C.+/–1 degree C. and Relative Humidity=50 percent +/–2 percent.

Test Procedure

1. Measure 50 grams +/–0.01 gram of saline solution into the 100 milliliter beaker.
2. Place the magnetic stir bar into the beaker.
3. Program the magnetic stir plate to 600 revolutions per minute.
4. Place the beaker on the center of the magnetic stir plate such that the magnetic stir bar is activated. The bottom of the vortex should be near the top of the stir bar.
5. Weigh out 2 grams +/–0.01 gram of the superabsorbent material to be tested on weighing paper.

Note: The superabsorbent material is tested as received (i.e. as it would go into an absorbent composite such as those described herein). No screening to a specific particle size is done, though the particle size is known to have an effect on this test.

6. While the saline solution is being stirred, quickly pour the superabsorbent material to be tested into the saline solution and start the stopwatch. The superabsorbent material to be tested should be added to the saline solution between the center of the vortex and the side of the beaker.
7. Stop the stopwatch when the surface of the saline solution becomes flat and record the time.
8. The time, recorded in seconds, is reported as Vortex Time.

Specific Volume ($SV_o$)

Specific Volume "SV" is a measure of the capacity or useable volume of a material at a given compressive load and is reported in cubic centimeters per gram of sample. SVo is the approximation of material capacity under zero compressive load. SVo is estimated by performing a regression analysis for the low load portion of the stress-strain relationship of a test material and can be computed with the use of an instrument such as an INSTRON 6021 apparatus which has been set to record displacement and load during a compression/recovery cycle. Specific volume measurements are made using samples of absorbent core material which are devoid of apertures 18 and high absorbency material 20.

Procedure

A two inch (5 centimeter) circular sample is cut, corresponding to the anvil set up on the instrument. The two inch stainless steel anvil has a smooth flat bottom which is removably attached to the cross beam of the INSTRON instrument.

After first recording the sample weight, the sample is placed on a flat stainless steel platen such that the sample is directly below the anvil. The gap between the anvil and the platen should be sufficient to allow the sample to be placed unrestricted into the test position. To accomplish this, the gap should be approximately 0.1 inch (2.5 millimeters) larger than the uncompressed sample to ensure accurate measurements in low compression situations.

The test cycle consists of at least one compression, where the anvil moves downwardly toward the platen, and one recovery cycle, where the anvil is raised back to its initial position. The movement of the anvil exerts force on the sample, compressing it until a stop load or stop distance is reached. During the compression and recovery cycle, the instrument will record the position of the anvil (displacement) versus the force applied against its load cell. The sample area is the sample radius squared multiplied by pi. Volume at a given load is calculated by multiplying the sample area (square centimeters) by the Sap-displacement (centimeters), and can be converted to specific volume by dividing by sample weight (grams). Specific volume is recorded for all loads throughout the test cycle. Compressive stress is calculated by dividing the measured force by the sample area.

The reciprocal of the cube of specific volume plotted on the x-axis against compressive stress on the y-axis has been shown to be linear at low compressive loads less than 35,000 dynes per square centimeter for these materials. Therefore, the regression analysis line for the curve of reciprocal volume cubed verus compressive stress is extended across the x-axis and the no load specific volume $SV_o$, is determined at the point of intersection between the regression line and the x-axis.

EXAMPLES

Example 1

In Example 1, an absorbent core was constructed using two layers of 108 grams per square meter two denier, fibrous through-air bonded side-by-side polypropylene/ polyethylene bicomponent spunbond nonwoven material. Each layer of the material had a density of 0.04 g/cc, a thickness of 0.25 centimeters, a Frazier air permeability of 108 m³/m²/min, a no load specific volume (SVo) of 25 cubic centimeters per gram and a third insult liquid intake rate of 6 milliliters per second using the FIFE test.

The two-layer absorbent core was cut to 10 centimeters by 36 centimeters and a plurality of circular apertures 1.3 centimeters in diameter were formed in the first 30 centimeters of the length of the material. The remaining 6 centimeters of the length of the sample were devoid of such apertures. The overall sample thus had 31% void space due to the apertures. The apertures were arranged in a staggered pattern and extended from the top surface of the first layer through to the bottom surface of the second layer. Thus the apertures in the two layers were in a vertical alignment with one another. A 75 grams per square meter liquid permeable hydroentangled pulp (HEP) sheet having the same dimensions as the absorbent core was then attached to the bottom surface of the absorbent core using what was estimated to be about 8 grams per square meter of National 34-5541 hot melt adhesive supplied by National Starch Company located in Bridgewater, New Jersey. The absorbent core/HEP sheet laminate was placed on a vacuum box with the HEP sheet side down and then about 9 grams of Favor 870 high absorbency material from Stockhausen Corporation located in Greensboro, North Carolina was uniformly sprinkled into the apertures. The high absorbency material had an absorbency under load (AUL) of about 18 gram per gram at 0.9 psi (6 kPa). The HEP bottom sheet not only contained the high absorbency material in the apertures, but also improved overall lateral liquid spreading in the absorbent core. A 21 gram per square meter liquid permeable barrier tissue sheet was then attached to the top surface of the absorbent core again using what was estimated to be about 8 grams per square meter of Cycloflex water-sensitive adhesive also supplied by the National Starch Company. The tissue structure was closed enough to prevent the particles of the high absorbency material from dusting or filtering out of the liquid-absorbing article.

The liquid-absorbing article described above was subject to the fluid run-off evaluation test. The average fourth insult liquid run-off was 5 grams as compared to 20 grams of runoff from a similar absorbent article constructed with wood fluff pulp as the absorbent core.

The high absorbency material was observed to swell vertically in the apertures of the absorbent core. As the vertical swelling increased, the top sheet separated from the absorbent core providing more room for the high absorbency material to swell and expand without exerting so much swelling force so as to rupture the top sheet.

Example 2

In Example 2 a liquid-absorbing article was constructed exactly as in Example 1 using the same two-layer apertured bicomponent spunbond absorbent core, top & bottom sheets, adhesive types and amounts. In addition, the same type of high absorbency material, Favor 870 superabsorbent from the Stockhausen Company, was used except that the total amount was reduced from 9 grams to 6 grams. The apertures were again 1.3 centimeters in diameter, vertically aligned and extended from the top through to the bottom surface of the two-layer bicomponent spunbond absorbent core.

The absorbent article had an increased average fourth insult liquid run-off of 25 grams using the fluid run-off evaluation test reflecting the reduced capacity of the absorbing article due to the reduction in the amount of the high absorbency material.

Example 3

In Example 3 a liquid-absorbing article was again constructed in the same way as in Example 1 above except the apertures were changed from 1.3 centimeter diameter circles to 2.5 centimeters ×1.3 centimeter oval shapes with rounded ends to provide the same 31% void space. The same top and bottom sheets, apertured bicomponent spunbond absorbent core, adhesive types and amounts, high absorbency material type and amount were also used. The absorbent article had a fourth insult liquid run-off of 18 grams using the fluid run-off evaluation test.

Example 4

In Example 4, an absorbent core was constructed in the same way as Example 1 except that it used two layers of 3 denier, 92 grams per square meter through-air bonded carded web material made from 100% polyethylene sheath/ polyester (PET) core bicomponent fibers produced by BASF Corporation located in Springfield, Va. Each layer of the material had a density of 0.03 grams per cubic centimeter, a thickness of 0.12 inches (0.3 cm), a Frazier air permeability of 238 $m^3/m^2/min$, a no load specific volume (SVo) of 36 cubic centimeters per gram and a third insult intake rate of 13 milliliters per second using the fluid intake and flowback evaluation test.

Apertures 0.6 centimeters in diameter were formed in the first 22 centimeters of length of the 10 centimeter by 36 centimeter carded web sample thereby providing a void space of approximately 20 percent. The apertures were arranged in a staggered pattern and, as in Example 1, extended through the web from the top to the bottom surface of the absorbent core in vertical alignment. A 22 gram per square meter liquid permeable barrier tissue was then attached to the bottom surface using what was estimated to be about 8 grams per square meter of the National 34-5541 hot melt adhesive. The absorbent core/tissue sheet laminate was placed with the tissue side down on a vacuum box and again a total of 9 grams of Favor 870 high absorbency material was sprinkled by hand into the apertures. A 17 gram per square meter standard tissue sheet was attached to the top surface using Cycloflex water-sensitive adhesive. The absorbent article had a fourth insult liquid run-off of 19 grams using the fluid run-off evaluation test.

Example 5

In Example 5, the absorbent article was constructed in the same fashion as Example 1 except that the absorbent core was a single layer of 390 gram per square meter air formed wood fluff pulp with a thickness of 0.2 inches (0.5 cm), a density of 0.09 grams per cubic centimeter, a Frazier air permeability of 11 $m^3/m^2/min$ and a no load specific volume (SVo) of 13.7 cubic centimeters per gram. The absorbent article had a fourth insult run-off of 20 grams using the fluid run-off evaluation test.

Based upon the experimentation, it was found in general that embodiments of the present invention in which the absorbent core comprised lofty, low density thermoplastic fibrous nonwoven materials tended to work better than absorbent cores containing wood pulp. The cores with wood pulp tended to collapse when wet resulting in reduced intake rates, less space for the superabsorbent particles and increased runoff on multiple insults. The two-layer bicomponent spunbond absorbent core in Example 1 with a plurality of 0.5 inch (1.3 cm) diameter apertures extending through from the top to the bottom surface of the core and providing approximately 31% void space worked quite well. Generally, the fibrous material areas surrounding the apertures in the absorbent core will have a density of less than 0.1 g/cc and preferably less than 0.08 g/cc for faster intake though materials with both lower and higher density regions may be adopted in specific applications to maximize both fluid intake and distribution. Frazier air permeability values for absorbent core materials as measured in the areas between the apertures should be at least 45 $m^3/m^2/min$ and preferably greater than 60 $m^3/m^2/min$ with a no load specific volume (SVo) value greater than about 18 cubic centimeters per gram and a target thickness of about 0.2 inches (0.5 cm) when measured at 0.05 psi (0.3 kPa) to provide enough aperture depth for high absorbency material containment and swelling. Although as in Example 1 more than one layer of the fibrous material may be used in the absorbent core, it is preferable to use one layer to minimize interface effects and to reduce material handling and processing costs. One layer of a fibrous absorbent core tested in the areas between the apertures will preferably have a third insult intake rate of at least 5 ml/sec using the fluid intake and flowback evaluation test. Examples 1 and 4 had good absorbency, with third insult intake rates greater than 6 ml/sec and 13 ml/sec respectively in the FIFE test. These results compare to less than 2 ml/sec in Example 5 in which wood fluff pulp was used to construct the absorbent core. Furthermore, the fourth insult using the fluid run-off evaluation in Example 1 was 5 grams compared to 20 gram in example 5. Although the present invention does not specify a limit on the fiber denier size of the absorbent core, generally the fiber sizes will be less than about 6 denier while in preferred executions the fiber sizes may be less than 3.5 denier or even 2.5 denier and below. Furthermore, absorbent cores with mixed fiber deniers may be adopted in specific applications. High absorbency materials with absorbency under load (AUL) values greater than about 15 g/g measured at 0.9 psi (6 kPa) seemed to work quite well. The top and bottom sheets have no real basis weight limits, though in cost effective product applications both sheets may be tissue with basis weights of about 20 grams per square meter. Basis weights lower than about 6 grams per square meter may not have adequate integrity and strength to prevent rupture. The top sheet in particular should have enough uniformity with pores generally smaller than the average particle size of the high absorbency material to prevent filtering-through of the high absorbency material to the wearer of the absorbent article. Furthermore, the attachment means should allow the separation of either the top or the bottom sheet from the absorbent core without rupturing either sheet by the forces exerted by the swelling high absorbency material. In such situations, however, the perimeter seal between the top and bottom sheet around the absorbent core should not separate.

Having thus described the invention in detail, it should be apparent that various modifications and changes can be made in the present invention without departing from the spirit and scope of the following claims.

We claim:

1. A liquid-absorbing article comprising:
a liquid-permeable top sheet and a bottom sheet with an absorbent core disposed therebetween, said absorbent core defining a plurality of apertures therein extending from a top surface through said absorbent core to a bottom surface, said top surface being attached to said top sheet and said bottom surface being attached to said bottom sheet, and a high absorbency material located within at least a portion of said apertures, and wherein either or both said top sheet and said bottom sheet are releasably attached to said absorbent core by attachment means, said attachment means providing a bond strength between said absorbent core and either said top sheet or said bottom sheet which is less than a swelling force exerted on said top sheet or said bottom sheet when said high absorbency material is exposed to an aqueous liquid such that said top sheet or bottom sheet will delaminate from said absorbent core before said top sheet or bottom sheet ruptures from said swelling force.

2. The liquid-absorbing article of claim 1 wherein said absorbent core has a first portion and a second portion, said first portion having a lower density than said second portion.

3. The liquid-absorbing article of claim 2 which further includes a personal care absorbent article comprising a bodyside liner and a backside liner with said liquid-absorbing article disposed between said bodyside liner and said backside liner.

4. The liquid-absorbing article of claim 1 which further includes a personal care absorbent article comprising a bodyside liner and a backside liner with said liquid-absorbing article disposed between said bodyside liner and said backside liner.

5. The liquid-absorbing article of claim 1 wherein said absorbent core in an area devoid of said plurality of apertures has a density of less than 0.08 grams per cubic centimeter.

6. The liquid-absorbing article of claim 5 wherein said absorbent core layer has a Frazier air permeability greater than 60 m$^3$/m$^2$/min.

7. The liquid-absorbing article of claim 6 wherein said absorbent core while under a pressure of 0.3 kilopascals has a thickness of at least 0.5 centimeters.

8. The liquid-absorbing article of claim 7 wherein said absorbent core has a specific volume at zero load which is greater than 18 cubic centimeters per gram.

9. The liquid-absorbing article of claim 1 wherein said absorbent core has a plurality of densified areas.

10. The liquid-absorbing article of claim 9 wherein said densified areas extend between and connect at least a portion of said plurality of apertures.

11. The liquid-absorbing article of claim 1 wherein said absorbent core is a fibrous nonwoven web.

12. The liquid-absorbing article of claim 11 wherein said web includes bicomponent fibers.

13. A liquid-absorbing article comprising:
a liquid permeable top sheet and a bottom sheet with an absorbent core disposed therebetween, said absorbent core including a first portion and a second portion in vertical registry with one another, said first portion being attached to said top sheet and defining a first plurality of apertures therein and extending therethrough and said second portion being attached to said bottom sheet and defining a second plurality of apertures therein and extending therethrough, at least a portion of said second plurality of apertures not being in vertical registry with said first plurality of apertures, said first plurality of apertures being filled with a high absorbency material and said secondary plurality of apertures being filled with a second high absorbency material, said high absorbency material having an absorption rate which is faster than said second high absorbency material.

14. The liquid-absorbing article of claim 13 wherein said first portion has a lower density than said second portion.

15. The liquid-absorbing article of claim 13 which further includes a personal care absorbent article comprising a bodyside liner and a backside liner with said liquid-absorbing article disposed between said bodyside liner and said backside liner.

16. A liquid-absorbing article comprising:
a liquid permeable top sheet and a bottom sheet with an absorbent core disposed therebetween, said absorbent core including a first portion and a second portion in vertical registry with one another, said first portion being attached to said top sheet and defining a first plurality of apertures therein and extending therethrough and said second portion being attached to said bottom sheet and defining a second plurality of apertures therein and extending therethrough, at least a portion of said second plurality of apertures not being in vertical registry with said first plurality of apertures, and a high absorbency material located within at least a portion of either or both of said first and second plurality of apertures, wherein either or both said top sheet and said bottom sheet are releasably attached to said absorbent core by attachment means, said attachment means providing a bond strength between said absorbent core and either said top sheet or said bottom sheet which is less than swelling force exerted on said top sheet or said bottom sheet when said high absorbency material is exposed to an aqueous liquid such that said top sheet or bottom sheet will delaminate from said absorbent core before said top sheet or bottom sheet ruptures from said swelling force.

17. The liquid-absorbing article of claim 16 wherein said first plurality of apertures are filled with a high absorbency material and said second plurality of apertures are filled with a second high absorbency material, said high absorbency material having an absorption rate which is faster than said second high absorbency material.

18. The liquid-absorbing article of claim 16 wherein said first plurality of apertures are filled with a high absorbency material and said second plurality of apertures are filled with a second high absorbency material, said high absorbency material having an absorption rate which is slower than said second high absorbency material.

19. A personal care absorbent article comprising:

a bodyside liner and a backside liner with a liquid-absorbing article according to claim 16 disposed between said bodyside liner and said backside liner.

20. A liquid-absorbing article comprising:

a liquid permeable top sheet and a bottom sheet with an absorbent core disposed therebetween, said absorbent core including a first portion and a second portion in vertical registry with one another, said first portion being attached to said top sheet and defining a first plurality of apertures therein and extending therethrough and said second portion being attached to said bottom sheet and defining a second plurality of apertures therein and extending therethrough, at least a portion of said second plurality of apertures not being in vertical registry with said first plurality of apertures, said first plurality of apertures being filled with a high absorbency material and said second plurality of apertures being filled with a second high absorbency material, said high absorbency material having an absorption rate which is slower than said second high absorbency material.

21. A personal care absorbent article comprising:

a bodyside liner and a backside liner with a liquid-absorbing article according to claim 20 disposed between said bodyside liner and said backside liner.

* * * * *